US006635042B2

United States Patent
Kumasaka

(10) Patent No.: US 6,635,042 B2
(45) Date of Patent: Oct. 21, 2003

(54) DISPOSABLE PANTS-TYPE DIAPER

(75) Inventor: Yoshinori Kumasaka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/981,408

(22) Filed: Oct. 17, 2001

(65) Prior Publication Data
US 2002/0045870 A1 Apr. 18, 2002

(30) Foreign Application Priority Data
Oct. 18, 2000 (JP) ........................................ 2000-317673

(51) Int. Cl.[7] .............................. A61F 13/15; A41B 9/00
(52) U.S. Cl. ........................................... 604/396; 2/400
(58) Field of Search ..................... 604/385.01, 385.201, 604/393–396; 2/78.1–78.4, 400–407

(56) References Cited

U.S. PATENT DOCUMENTS 3,710,797 A    1/1973   Marsan
5,864,890 A    2/1999   Niedermeyer
6,293,936 B1 * 9/2001   Otsubo ........................ 604/396

FOREIGN PATENT DOCUMENTS

JP    6-57502       3/1994
WO    WO 00/33679   6/2000

* cited by examiner

Primary Examiner—Weilun Lo
Assistant Examiner—Catherine L. Anderson
(74) Attorney, Agent, or Firm—Butzel Long

(57) ABSTRACT

A disposable pants-type diaper is composed of a pair of sheets each having longitudinally opposite end portions extending in a transverse direction and transversely opposite side edge portions extending in a longitudinal direction. The pair of sheet are bonded together in desired zones including the transversely opposite side portions to form a disposable pants-type diaper. The pair of sheets are placed upon each other so that one of the transversely opposite side edge portions is destined to lie on a belly side of the diaper and the other thereof is destined to lie on the rear side of the diaper.

3 Claims, 3 Drawing Sheets

DISPOSABLE PANTS-TYPE DIAPER

BACKGROUND OF THE INVENTION

This invention relates to a disposable pants-type diaper.

Japanese Patent Application Publication No. 1994-57502A describes a disposable pants-type diaper comprising a pair of sheets being identical in shape as well as in size, each having longitudinally opposite upper and lower end portions and transversely opposite side edge portions, these sheets being placed upon each other and bonded together along the transversely opposite side edge portions and in the middle sections of the lower end portions thereof to form a waist-opening and a pair of leg-openings. The transversely opposite side edge portions of these two sheets are joined to each other to define transversely opposite side edge portions of the diaper extending in the longitudinal direction. One of these two sheets forms a front waist region and the other forms a rear waist region of the diaper.

The pants-type diaper of prior art disclosed in the Publication is flatly stretched in the transverse direction and, even if a baby's mother or other helper attempts to widen the waist-opening with both her hands put into the waist-opening in order to spread out in applying the diaper onto the baby's body, it will be difficult to widen the leg-openings sufficiently. Consequently, pulling baby's legs into the respective leg-openings may take much time.

SUMMARY OF THE INVENTION

It is an object of this invention to provide a disposable pants-type diaper designed so that the leg-openings can be sufficiently widened in applying the diaper onto a wearer's body.

According to this invention, there is provided a disposable pants-type diaper comprising a pair of sheets being identical to each other in shape as well as in size, each having longitudinally opposite upper and lower end portions extending in a transverse direction and transversely opposite side edge portions extending in a longitudinal direction, the pair of sheets being placed upon and bonded to each other in predetermined zones including the transversely opposite side portions to form a waist-opening and a pair of leg-openings.

The disposable pants-type diaper further comprises the pair of sheets extending in parallel to each other in a plane extending in front and rear side directions of the diaper with one of the transversely opposite side edge portions defining a front side edge portion destined to lie on a belly side of the diaper and the other of the transversely opposite side edge portions defining a rear side edge portion destined to lie on a rear side of the diaper so that the upper edge portion constitutes with upper sections of the front and rear side edge portions half a circumference of a waist region of the diaper and lower sections of the front and rear side edge portions constitute with the lower end portion each of the leg-openings and a leg region surrounding the leg-opening. The waist region has a first center line bisecting a dimension between the upper sections of the front and rear side edge portions, the leg region has a second center line bisecting a dimension between the lower sections of the front and rear side edge portions longer than that between the upper sections wherein the second center line lies closer to the rear side of the diaper compared to the first center line. The pair of sheets folded back onto themselves along the second center line and an extension thereof have the front side edge portions and the rear side edge portions overlaid together, respectively, and are bonded to each other along these front and rear side edge portions in this manner to define the waist-opening and the pair of leg-openings.

DETAILED DESCRIPTION OF THE PREFERRED EMBODIMENTS

Details of the disposable pants-type diaper according to this invention will be more fully understood from the description given hereunder with reference to the accompanying drawings.

Figure 1:
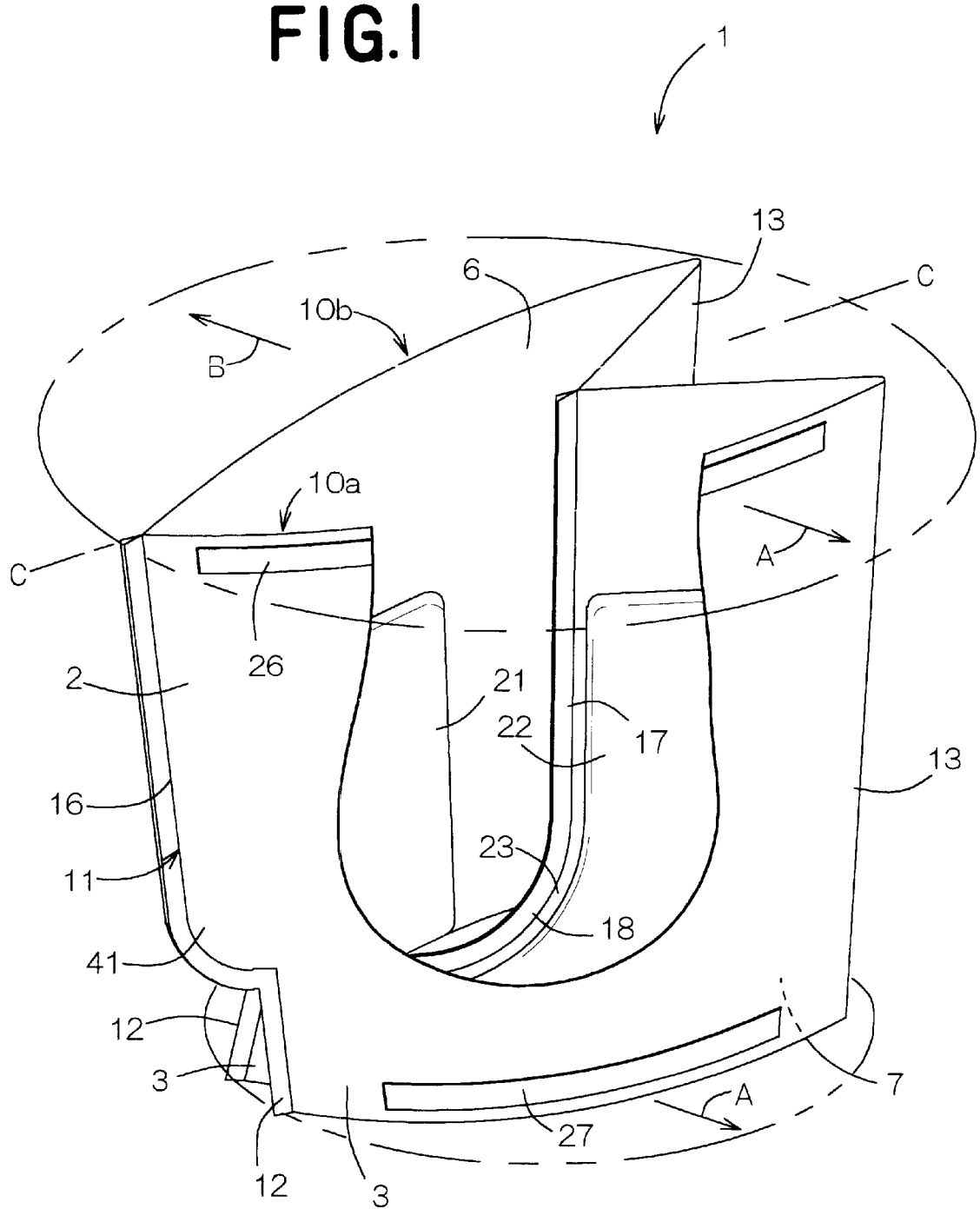
FIG. 1 is a perspective view of a disposable pants-type diaper according to this invention.

A disposable pants-type diaper 1 shown by FIG. 1 in a perspective view as partially broken away is of a trunks-type and comprises a pair of sheet members 10a, 10b lying on both sides about a center line C—C bisecting the width of the diaper 1. The diaper 1 is composed of a waist region 2 and a pair of leg-regions 3 extending downward from the waist region 2 wherein the waist region 2 is formed at its upper end with a waist-opening 6 and the leg-regions 3 are formed at lower ends thereof with a pair of leg-openings 7, respectively. Referring to FIG. 1, the diaper 1 is folded along a first bonding line 11 formed in the waist region 2, a pair of bonding lines 12 (See FIGS. 2 and 3) formed in the respective leg-regions 3 and a pair of folding lines 13 extending from the waist region 2 to the leg-regions 3 on a rear side of the diaper 1 so that the diaper 1 may be flattened in a plane extending in front and rear side directions of the diaper 1. In applying the diaper 1 on a baby's body, his or her mother may put both her hands into a waist-opening 6 and expand the diaper 1 transversely in opposite directions indicated by arrows A, B until the waist-opening 6 as well as the leg-openings 7 are expand roundly by so that the baby's legs may be easily brought into the respective leg-openings 7. The first bonding line 11 comprises a section 16 vertically extending so as to bisect a belly side of the waist region 2 in a direction of its width, a section 17 vertically extending so as to bisect a rear side of the waist region 2 and a section 18 connecting these two sections 16, 17 in the crotch region. Along these sections 16–18 of the first bonding line 11, the sheet members 10a, 10b are placed upon and adhesively bonded or heat welded to each other. These waist and leg regions 2, 3 are provided along the section 18 of the first bonding line 11 on the inner surfaces thereof with a body fluid absorbent pad, for example, comprising first and second pads 21, 22 as in the illustrated embodiment. The waist-opening 6 and the leg-openings 7 may be provided, if necessary, along peripheral edge portions thereof with elastic members 26, 27, respectively, bonded under tension in the circumferential direction thereto so that the diaper 1 may fit tightly to the wearer's skin.

Figure 2:
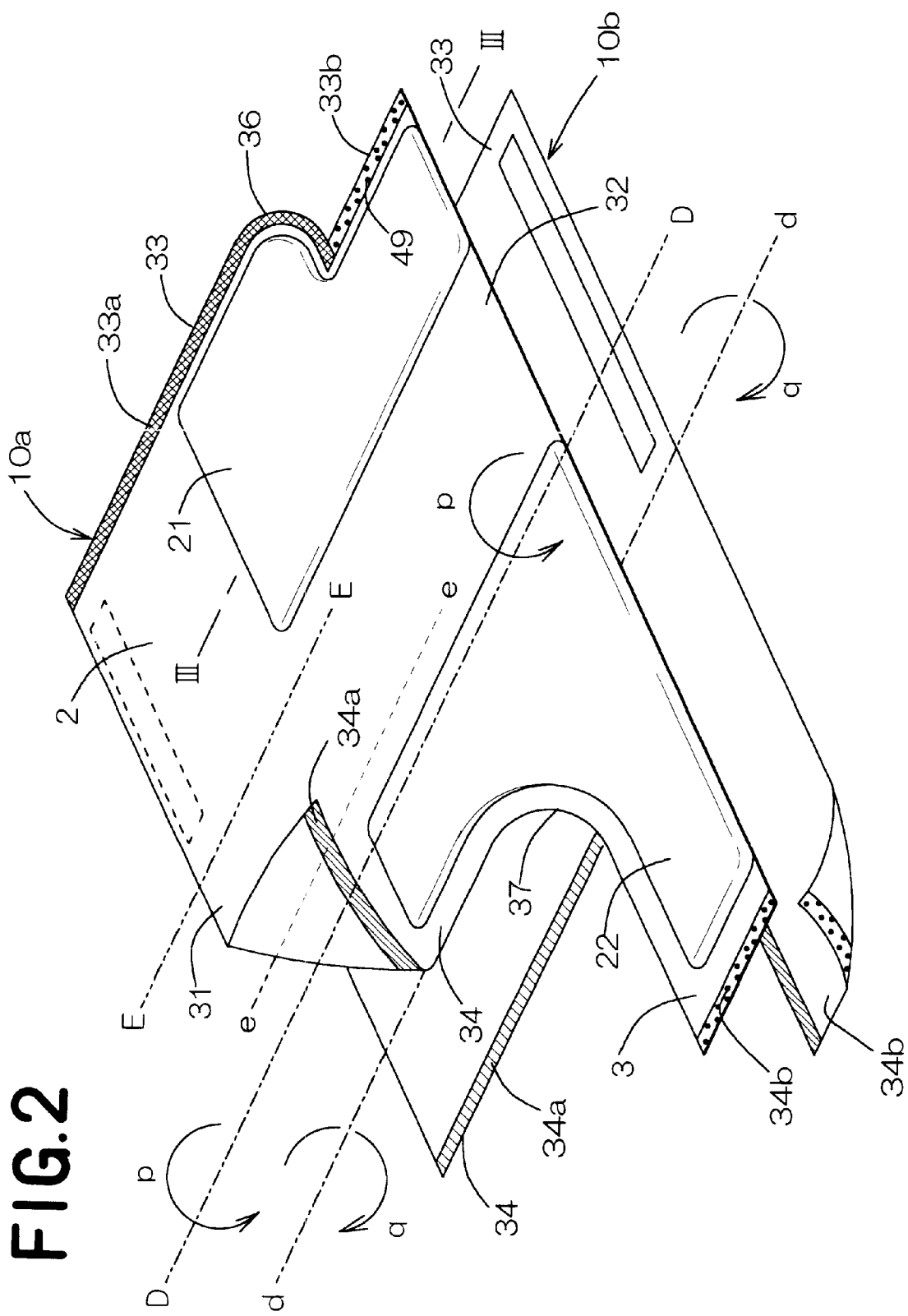
FIG. 2 is a perspective view of the unfolded sheet members.

FIG. 2 is a perspective view showing the sheet members 10a, 10b separated from each other along the first and second bonding lines 11, 12 and then reversed along the folding lines 13. The sheet members 10a, 10b are identical to each other in shape as well as in size and extend in parallel to each other in the plane extending in front and rear side directions of the diaper 1. Each of the sheet member 10a, 10b is contoured by longitudinally opposite upper and lower end portions 31, 32 horizontally extending and transversely opposite front and rear side edge portions 33, 34 vertically extending. The front side edge portion 33 lies on the left side of the rear side edge portion 34 when the diaper 1 is in the state of FIG. 1 and lies on the right side of the rear side edge potion 34 when the diaper 1 is in the state of FIG. 2.

The sheet member 10a of the sheet member 10a, 10b will be explained more in detail with reference to FIG. 2. The front and rear side edge portions 33, 34 of the sheet member 10a, 10b have front and rear upper sections 33a, 34a destined to define the waist region 2 and front and rear lower sections 33b, 34b destined to define the leg regions 3. Specifically, the waist region 2 is defined by the front and rear upper sections 33a, 34a and the upper end portion 31 and the leg regions 3 are defined by front and rear lower sections 33b, 34b and the lower edge portion 32. A single-dotted chain line D—D indicates a line extending in the vertical direction of the diaper 1 so as to bisect a horizontal dimension of the lower edge portion 32, i.e., a dimension between the lower sections 33b, 34b of the front and rear side edge potions. The line D—D corresponds to the folding line 13 in FIG. 1 along which the sheet member is folded to shape the diaper 1 in the trunks-type. A double-dotted chain line E—E in FIG. 2 indicates a line vertically extending so as to bisect a horizontal dimension of the upper end portion 31 lies aside toward the right side of FIG. 2 with respect to the single-dotted chain line D—D. As will be apparent from the relative position of these single-dotted chain line D—D and double-dotted chain line E—E, the leg-regions 3 lie aside toward the rear side edge portion 34 with respect to the waist region 2, i.e., toward the rear side of the diaper 1. The lower sections 33b, 34b of the front and rear side edge portions 33, 34, respectively, are in a symmetric relation about the single-dotted chain line D—D and, in the illustrated embodiment, in parallel to the single-dotted chine line D—D. While the upper sections 33a, 34a of the front and rear side edge portions 33, 34 are different from the lower sections 33b, 34b in that these portions may be selectively configured, the upper section 33a preferably includes a curved section 36 which is convex outward immediately above the lower section 33b and the upper portion 34a of the rear side edge portion 34 preferably includes a curved section 37 which is convex inward immediately above the lower portion 34b of the rear side edge portion 34, as in the illustrated embodiment. The sheet member 10a is provided on its surface destined to define the inner surface of the waist-shaped diaper 1 with body fluid absorbent first and second pads 21, 22 attached thereto. The first pad 21 is centered at the curved section 36 of the front side edge portion 33 and extends to the upper and lower sections 33a, 33b and the second pad 22 is centered at the curved section 37 of the rear side edge portion 34 and extends to the upper and lower portions 34a, 34b.

While the sheet member 10b is identical to the sheet member 10a in size as well as in shape as has been described, the sheet member 10b is in back to back relationship with the sheet member 10a. Accordingly, the first and second pads 21, 22 are attached to the lower surface of the sheet member 10b as viewed in FIG. 2. The sheet member 10b has a single-dotted chain line d—d and a double-dotted chain line e—e corresponding to the single-dotted chain line D—D and the double-dotted chain line E—E of the sheet member 10a, respectively.

Figure 3:
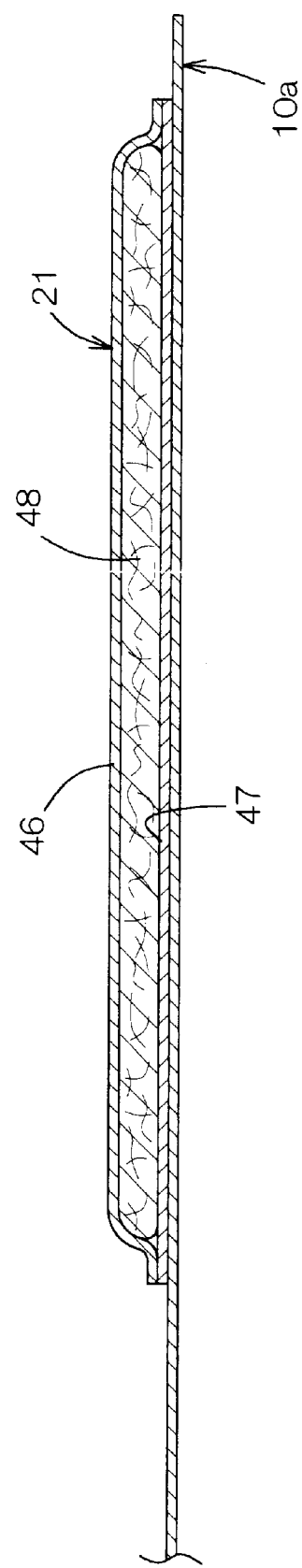
FIG. 3 is a sectional view taken along a line III—III in FIG. 2.

FIG. 3 is a fragmentary sectional view of the sheet member 10a as taken along a line III—III in FIG. 2. The first pad 21 comprises a liquid-pervious inner sheet 46, a liquid-impervious outer sheet 47 and a core 48 made of water-absorbent material such as fluff pulp or a mixture of fluff pulp and highly water-absorbent polymers and disposed between the two sheets 46, 47. These two sheets 46, 47 are bonded together along portions thereof extending outward beyond a peripheral edge of the core 48. The outer sheet 47 is attached to the inner surface of the sheet member 10b by means of hot melt adhesive (not shown).

To obtain the diaper 1 of FIG. 1 from the sheet members 10a, 10b as has been described above, such steps as described below may be followed. First, the sheet members 10a, 10b in FIG. 2 are folded back onto themselves in the directions indicated by arrows p and q along the single dotted chain lines D—D and d—d, respectively. Then, the lower sections 33b, 34b of the front and rear side edge portions 33, 34, which are in symmetric relationship, are overlaid and adhesively bonded or heat welded to each other in such zones as indicated by a plurality of dots 49. Then, the sheet members 10a, 10b are placed upon each other with their upper edge portions 31 and lower edge portions 32 as well as their upper sections 33a of the front side edge portions 33 overlapped, respectively. The upper sections 34a of the respective rear side edge portions 34 are adhesively bonded or heat welded to each other in hatched zones and the upper sections 34a of the respective rear side edge portions 34 are adhesively bonded or heat welded to each other in reticulated zones. In this manner, the sheet members 10a, 10b are assembled into the diaper 1 of FIG. 1. In the diaper 1 for a boy, the sheet members 10a, 10b may be bonded together along the curved sections 36 of the respective front side edge portions 33 to form a bulged portion 41 (See FIG. 1) adapted to accommodate boy's penis.

To implement this invention, the sheet members 10a, 10b except the first and second pads 21, 22 are preferably formed with breathable but liquid-impervious sheets having an elastic stretchability in a waist-surrounding direction. It is also possible without departing from the scope of this invention to form these sheet members 10a, 10b using non-stretchable sheets or laminated sheet consisting of liquid-impervious plastic film and nonwoven fabric. Such nonwoven fabric forming the inner surface and/or the outer surface of the diaper 1 enables the diaper 1 to offer a cloth-like touch. In the illustrated embodiment, the peripheral edge portions of the waist-opening 6 and the leg-openings 7 are partially provided with elastic members 26, 27 each having a length and a width which may be selectively dimensioned. Area as well as thickness of the first and second pads 21, 22 also may be selectively dimensioned. It is also possible without departing from the scope of this invention to realize these pads 21, 22 in the form of a single pad by eliminating one of these pads 21, 22.

The disposable pants-type diaper can be made merely by bonding a pair of the sheet members being identical to each other in shape as well as in size. This feature simplifies its production and enables the diaper to be folded along the bonding line serving also as the guide line bisecting the diaper in its transverse direction and thereby to be flattened in the plane extending in back and forth direction of the diaper 1. For example, the wearer's mother may open the diaper in its transverse direction with her both hands inserted into the inside of the diaper so that the waist-opening as well as the leg-openings may be expanded and the diaper may be easily put on the baby's body.

What is claimed is:

1. A disposable diaper comprising:
   a center line that bisects the diaper into a left and a right half which cover left and right sides of a wearer of the diaper respectively;
   a waist portion that encircles a waist of the wearer of the diaper;

a pair of leg portions that extend downwardly from left and right halves of the waist portion respectively to encircle legs of the wearer of the diaper;

a waist opening provided at the top of the waist portion; and a pair of leg openings provided on the bottom of the leg portions respectively, the left and right halves of the waist portion are defined by a pair of sheets that are identical to each other in shape and size and have an inside surface that is contactable with wearer's skin, and an outside surface that is contactable with the wearer's clothes, each of the sheets comprising:

front and rear ends;

an upper edge portion that extends transversely between the front and rear ends, which upper edge portion defines an edge portion of either the front or right half of the waist opening;

a lower edge portion that extends transversely between the front and rear ends and is parallel and displaced forward with respect to the upper edge portion, the lower edge portion defining an edge portion of one of the lag openings;

upper front and rear edge portions that extend downwardly from front and rear ends of the upper edge portion respectively;

lower front and rear edge portions that extend upwardly from front and rear ends of the lower edge portion respectively;

a front intermediate connecting edge portion running between a lower end of the upper front edge portion and an upper end of the lower front edge portion; and a rear intermediate connecting portion running between a lower end of the upper rear edge portion and an upper end of the lower rear portion, each of the sheets being folded inside onto itself along a line that bisects the lower edge portion between the front and rear ends and attached to itself along the front and rear edge portions so as to provide one of the leg holes, each of the sheets, when folded, being placed on each other and attached between the respective inside surfaces of the upper front edge portions and between the respective outside surfaces of the upper rear edge portions.

2. The disposable pants-type diaper according to claim 1, wherein said pair of sheets are elastically expandable in a waist-surrounding direction of the pants.

3. The disposable pants-type diaper according to claim 1, wherein a body fluid absorbent pad covered with a liquid-pervious sheet is attached to a portion of an inner surface of said pants.

* * * * *